United States Patent [19]

Almeida

[11] 4,190,645

[45] Feb. 26, 1980

[54] ROTAVIRUS INNER CAPSID SUBUNIT PREPARATIONS

[75] Inventor: June D. Almeida, London, England

[73] Assignee: Burroughs Wellcome Co., Research Triangle Park, N.C.

[21] Appl. No.: 938,230

[22] Filed: Aug. 30, 1978

Related U.S. Application Data

[63] Continuation-in-part of Ser. No. 838,219, Sep. 30, 1977, abandoned.

[30] Foreign Application Priority Data

Sep. 30, 1976 [GB] United Kingdom ............... 40608/76

[51] Int. Cl.² .................... A61K 39/12; C12K 7/00
[52] U.S. Cl. .................................. 424/89; 435/317; 435/236
[58] Field of Search ........................... 424/89; 495/1.5

[56] References Cited

PUBLICATIONS

Rodgers et al., Chem. Abst. vol. 87 (1977) p. 180,409t.
Newman Nature, vol. 258 (Dec. 18, 1975) pp. 631–633.

*Primary Examiner*—Sam Rosen
*Attorney, Agent, or Firm*—Donald Brown

[57] ABSTRACT

A preparation of rotavirus inner capsid antigenic subunits which is substantially free from complete virus particles and fragments thereof. The subunits have a sedimentation coefficient of 17.5S, and a molecular weight of $>2\times10^5$ and $>2\times10^6$. Such a preparation can be prepared by suspending a sample of faecal material obtained from a mammal infected with rotavirus, incubating the suspension followed by the removal and concentration of the subunits from the suspension by centrifugation and/or filtration. Such a preparation is useful in several immunological tests and for the preparation of antisera also for use in tests.

8 Claims, No Drawings

ROTAVIRUS INNER CAPSID SUBUNIT PREPARATIONS

This applicatin is a continuation in part of Ser. No. 838219 filed Sept. 30, 1977 now abandoned.

This invention relates to the diagnosis of gastroenteritis caused by rotavirus, and in particular to preparations of rotavirus suitable for use as a diagnostic reagent in immunological test systems.

Rotavirus particles were first discovered in the stools of scouring calves by Ferneluis, A. L. et al in Archiv für die Gesamte Virusforschung, 1972, 37, 114–130 and were designated rotavirus because of their wheel-like appearance under the electron microscope. Subsequently it has been established that particles of identical morphology can be found in the faeces of other species, for example pigs and humans, and that they are invariably associated with gastroenteritis. Indeed, rotavirus is considered to be one of the chief causal agents in infantile gastroenteritis.

Superficially the particles resemble reovirus, in that they have an outer capsid and an inner capsid, the diameters of which are 70 nm and 55 nm respectively (Flewett, T. H. et al J. Clin. Path., 1974, 27, 603–614), the double shelled capsid surrounds an inner protein shell or core which contains the nucleoprotein. The particles are, however, morphologically distinct from reovirus since the subunits in the outer of the two capsids have a smooth, or continuous, outer surface.

After the discovery of the rotavirus group it was shown that serological relationships existed between the viruses associated with different species (Kapikian, A. Z. et al, *Science*, 1974, 185, 1049–1053). Indeed, it was also shown by Kapikian, A. Z. et al in Lancet, 1975, 1, 1056–1061 that it is possible to use virus isolated from the faeces of scouring calves as a diagnostic antigen in studying human rotavirus infection. More recently it has been shown that serological crossing between members of the rotavirus group is, for the most part, mediated by the antigens of the inner capsid, (Woode, G.N. et al, *Infection* and *Immunity* in press).

Newman et al, in *Nature*, 258, 631–633, (1975), demonstrated the pesences in cultures of rotavirus of whole rotavirus particles and rotavirus particles without their outer capsid layer, by density gradient centrifugation on caesium chloride. In order to study the virus further, in particular the polypeptides making up the virus, Newman and his co-workers treated the virus with urea and sodium dodecasulphate, the latter being a detergent which completely breaks up the virus, thus destroying all the antigenicity of the virus or the subunits thereof.

It has now been discovered that preparations of rotavirus infected faeces may contain considerable amounts of the inner capsid in the form of antigenic viral subunits, and that the relative proportion of such subunits can be increased by appropriate treatment.

According to the present invention in one aspect, therefore, there is provided a rotavirus inner capsid antigenic subunit preparation and substantially free from complete virus particles and fragments thereof.

The subunit, when viewed in the electron microscope, is generally circular in shape, with a diameter of 50 Å and a 15 Å hole in the centre. It is chiefly comprised of protein which contains little or no carbohydrate. Unlike the external capsid, the inner capsid subunit is not agglutinated by plant lectins such as conavalin A.

By sedimentation in 5–25% sucrose gradients the subunit can be demonstrated to have a sedimentation coefficient of 17.5S, using poliovirus and IgM as size markers. By using sepharose 6B gel filtration, and sephadex G200 filtration the molecular weight of the subunit has been found to be $>2 \times 10^5$ and $<2 \times 10^6$.

According to a second aspect of the invention there is provided a method for preparing and concentrating rotavirus inner capsid subunits which comprises suspending a sample of faecal material obtained from a mammal infected with rotavirus, incubating the suspension at 30° to 45° C. for at least 20 minutes, removing and concentrating the subunits from the suspension by centrifugation and/or filtration.

In order to obtain a preparation of rotavirus subunits, faecal material can be obtained from a mammal infected with rotavirus as demonstrated by immune electron microscopy using convalescent serum from the mammal, such mammals include calves, pigs, mice or children. The faecal material is suspended in a suitable buffer, at a pH of between 5 and 9 so as to form a suspension of from 5 to 30%, preferably about 20% by weight. The suspension is then placed in a closed container and incubated at a temperature of between 30° and 45° C., preferably about 37° C. for at least 20 minutes, usually 30 minutes. The suspension is then clarified preferably by centrifuging at a speed sufficient to sediment whole virus particles and fragments, but insufficient to sediment the subunits. The supernatent is then filtered and the resultant fluid, which is almost clear, is concentrated at least 10 times, but preferably 25 times, preferably by either Minicon or Amicon (Amicon Corp.) molecular filtration concentration methods.

The subunit concentrate produced by this method can be further purified by density gradient centrifugation, for example using a sucrose gradient. Furthermore it may be possible to increase the proportion of subunits in the concentrate by treating the initial faecal suspension with enzymes, such as trypsin or papain, which may break down the complete virus particles into their component subunits. For instance a concentration of 0.5% trypsin may be employed for 1 hour at 37° C.

The presence of viral subunits in the concentrate can be demonstrated by direct negative staining electron microscopy, or immune electron microscopy which is preferred. When examined using immune electron microscopy, preparations consist almost entirely of circular, fuzzy-edged subunits, whose size is less than 2 nm, complexed with antibody. One or two complete virus particles about 70 nm in diameter or large fragments thereof, may also be visible.

The subunit concentrate according to the present invention can be used in several immunological diagnostic tests, such as immune electron microscopy, immunodiffusion, haemagglutination, complement fixation and radioimmunoassay.

Immune electron microscopy can be used to diagnose the cause of gastroenteritis in a patient, or determine whether or not an individual has recently suffered from, or is experiencing a subclinical infection. In order to perform such a test a subunit concentrate is prepared as described above and admixed with a sample of serum taken from the patient, allowed to interact at room temperature and then centrifuged. The supernatant is discarded and the pellet is negatively stained with phosphotungstate and then examined under the electron microscope for the presence of subunits complexed with antibody.

For immunodiffusion, a suitable gel is prepared as a layer on a plate in which equal sized, equally spaced holes are cut. Into some of the holes subunit concentrate is placed and in the others test serum from the patient, the gel is then left at room temperature for a few hours and then examined for reaction. Where rotavirus specific antibodies are present in the test serum a precipitin line will form in the gel where the serum diffusing into the medium meets the subunits which have also diffused. Using suitably placed reference antigen and antisera, the immunodiffusion test can be successfully used to screen serum samples from patients for the presence of antibody, or faecal extracts for viral antigen. The subunit concentrate is particularly advantageous in gel diffusion tests since the subunits have been found to have much greater mobility in the gel, over the complete viruses as demonstrated by the lack of any other precipitin line representing the complex of whole virus and antibodies and therefore the subunits migrate rapidly through the gel so that the results can be read more quickly, and with more certainty.

Using the established technique of complement fixation as described by Bradstreet & Taylor in *Public Health Laboratory Services Bulletin,* 1962, 21, 96, the subunit concentrate can be used for diagnosing rotavirus infections.

To perform a haemagglutination test it may be possible to artificially attach the subunits to red cells and then incorporate such red cells into a haemagglutination test system, as described for example by Sequeira, P. J. L., and Eldridge, A. E. in *Br. J. Vener. Dis.,* 1973, 49, 3, or even incorporate them into a gel system to which antiserum and complement can be added.

One advantage of the subunit concentrate is that since the serological relationships occurring between members of the rotavirus group are mediated by the antigens of the internal component, it can react equally well with homologous and heterologous antisera thus providing a valuable general diagnostic tool. Additionally the subunit concentrate can be prepared from faecal samples quite easily by simple laboratory techniques and then tested using reference serum known to contain antibodies to rotavirus. In this way all the tests described previously can be used to test faecal samples for rotavirus by employing rotavirus antiserum.

According to a third aspect of the invention there is provided a preparation of rotavirus antiserum containing antibodies to the rotavirus inner capsid subunit.

In yet a further aspect of the invention there is provided a method of preparing a rotavirus antiserum containing antibodies to the rotavirus inner capsid subunit, which method comprises injecting a mammal with a preparation of rotavirus inner capsid subunit, after several days injecting the mammal with a second aliquot of the subunit preparation, the mammal being bled after a further few days, the blood being left to clot allowing the antiserum to be separated and removed.

Further advantages of the present invention will become apparent from the following description of the embodiments of the invention, which embodiments, however, do not limit this invention in any way.

EXAMPLE 1—Preparation of subunit concentrate

Faecal material was obtained from infected calves from a dairy herd in which an outbreak of rotavirus infection had occurred. A 20% suspension of faecal material was made in phosphate buffered saline (PBS). The suspension was placed in a firmly covered tube and maintained at 37° C. in a water bath for 30 minutes. During this period the suspension was mixed thoroughly at least 3 times using a mechanical mixer. The mixture was then clarified by centrifuging for 15 minutes at 3000 g.

The supernatent from this stage was passed through a Millipore prefilter plus 1.2 $\mu$m filter. The resultant fluid, which was almost clear, was then placed in a Minicon B15 (manufactured by Amicon Corp.) and concentrated 25 times. Using this method, 1ml. of faeces yields 0.2 ml. of the preparation as a final concentrate.

EXAMPLE 2—Diagnosis by Immune electron microscopy

Aliquots (0.5 ml) of the subunit concentrate as prepared in Example 1 were placed in tubes and bovine or human serum (0.1 ml.) obtained from individuals suffering from gastroenteritis was added to each tube, and standard saline solution (0.1 ml) was added to a control tube. The tubes were left at room temperature for one hour and then centrifuged for one hour at 12,000 g. The supernatent was discarded and the pellets were negatively stained using phosphotungstic acid in the usual manner. On examining under the electron microscope aggregates of small, circular subunits complexed with antibody were seen, demonstrating that the patients' gastroenteritis was caused by rotavirus.

EXAMPLE 3—Diagnosis by Immunodiffusion

A patient suffering from gastroenteritis provided samples of blood from which serum was prepared.

Agarose was made up in TRIS/EDTA buffer, consisting of 0.9% w/v agarose, and an aliquot (2 ml.) was used to cover a glass slide. A template of two rows 3 mm holes and 3 mm spacing was used to cut holes in the gel. One row of the holes were filled with subunit concentrate as prepared in Example 1, and the other row of holes were filled with serum from a patient suffering with gastroenteristis. After filling the gel was left overnight at room temperature.

When the gel was examined the following day it was found that a line of precipitin had formed in the gel between the holes containing subunit concentrate and those containing the patient's serum, which indicates that the gastroenteristis from which the patient was suffering was caused by rotavirus.

Example 4—Diagnosis by Complement Fixation Test

Human sera to be tested for the presence of antibodies to rotavirus were first diluted 1:2 in veronal buffered saline (VBS) and heat inactivated in a water bath maintained at 56° C. for 30 min. These sera were then titrated across a "U" bottomed microtitre plate from 1:2 to 1:256 dilutions in VBS using 0.025 ml amounts. Each serum was titrated in two parallel rows. To the first dilution series 0.025 ml volumes of rotavirus subunit preparation at a dilution of 1:8 in VBS was added. The second dilution series was used as an antiserum control and 0.025 ml VBS was added to the sera in place of the antigen. An antigen control was also included, antigen being added to 0.025 volumes of VBS without the addition of test serum.

Complement, stored at −70° C. was diluted to 1:50 in VBS and 0.025 ml volumes added to all of the wells. A complement control was added in the usual way. The plate was then covered and left at 4° C. overnight.

On the following day antiserum against sheep red blood cells, i.e., haemolytic serum, which is stored at −20° C. was diluted from 1:100 to 1:800 in VBS and incubated with an equal volume of 4% sheep red blood cells at 37° C. for 30 mins. to form a haemolysin system. At the same time the plate was transferred to 37° C. so that all of the components of the system would be at the same temperature. 0.025 ml volumes of the haemolysin system were added to each well and the plate gently shaken. The plate was further incubated at 37° C. for ½ hr. and was shaken at 15 min. intervals. It was then replaced at 4° C. for 2–3 hrs. before being read.

Where lysis of the red blood cells had occurred, this indicated the presence of antibodies to rotavirus in the test serum sample.

EXAMPLE 5—Preparation of Antiserum to Rotavirus inner capsid subunit

Rotavirus inner capsid subunit preparation (2 ml) was mixed with an equal volume of Freund's complete adjuvant and split into 2 aliquots of 2 ml. One aliquot was administered subcutaneously to 2 guinea pigs. Twenty-one days later the second aliquot was administered by the same route to the guinea pigs. Thirty-five days after the first administration the guinea pigs were bled out and the blood was left to clot. The fluid recovered after clotting was completed in antiserum to rotavirus inner capsid subunits.

I claim:

1. A rotavirus inner capsid antigenic subunit preparation substantially free from complete virus particles and fragments thereof, wherein the subunits have a sedimentation coefficient of 17.5S, and a molecular weight of $>2\times 10^5$ and $<2\times 10^6$.

2. A preparation as claimed in claim 1 wherein the subunits are circular in shape, when viewed in the electron microscope, with a diameter of 50 Å and a 15 Å hole in the centre.

3. A method for preparing a rotavirus inner capsid subunit preparation as claimed in claim 1 or claim 2 comprising suspending a sample of faecal material obtained from a mammal infected with rotavirus, incubating the suspension at 30° to 45° C. for at least 20 minutes, removing and concentrating the subunits from the suspension by centrifugation and/or filtration.

4. A method as claimed in claim 3 wherein the faecal material is suspended in a buffer at a pH of from 5 to 9.

5. A method as claimed in either claim 3 or claim 4 wherein the suspension is incubated at about 37° C.

6. A method as claimed in any one of claims 3, 4 or 5 wherein the subunits are removed from the suspension by centrifugation at a speed sufficient to sediment whole virus particles and fragments, but insufficient to sediment the subunits.

7. A method as claimed in any one of claims 3, 4, 5 or 6 wherein the initial faecal suspension is incubated with a proteolytic enzyme.

8. A method as claimed in claim 7 wherein the proteolytic enzyme is trypsin or papain.

* * * * *